United States Patent [19]

Hucks et al.

[11] 4,356,129
[45] Oct. 26, 1982

[54] PROCESS FOR THE PREPARATION OF NEUTRAL PHOSPHOROUS ACID ARYL ESTERS

[75] Inventors: Uwe Hucks, Alpen; Erhard Tresper; Claus Wulff, both of Krefeld, all of Fed. Rep. of Germany

[73] Assignee: Bayer Aktiengesellschaft, Leverkusen, Fed. Rep. of Germany

[21] Appl. No.: 213,136

[22] Filed: Dec. 4, 1980

[30] Foreign Application Priority Data

Dec. 17, 1979 [DE] Fed. Rep. of Germany ....... 2950694

[51] Int. Cl.³ .............................................. C07F 9/141
[52] U.S. Cl. ..................................... 260/973; 260/976
[58] Field of Search ........................ 260/973, 974, 976

[56] References Cited

U.S. PATENT DOCUMENTS

| 2,450,903 | 10/1948 | Mikeska | 260/976 |
| 3,463,838 | 8/1969 | Hensel et al. | 260/976 |
| 3,494,986 | 2/1970 | Hechenbleikner | 260/976 |
| 3,689,602 | 9/1972 | Ismail | 260/976 |
| 4,290,977 | 9/1981 | Hucks et al. | 260/973 |

Primary Examiner—Anton H. Sutto

Attorney, Agent, or Firm—Sprung, Horn, Kramer & Woods

[57] ABSTRACT

A process for the preparation of a neutal phosphorous acid aryl ester of the general formula

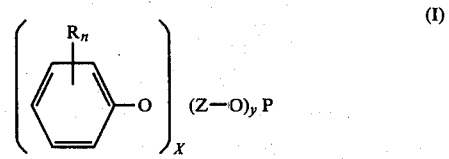

wherein a phosphorus trihalide, phosphorus acid monoester dihalide or phosphorous acid diester halide is reacted with a hydroxyaryl compound wherein an excess of hydroxyaryl compound and an excess of aqueous alkali metal hydroxide solution or suspension or alkaline earth metal hydroxide solution or suspension are employed, relative to the phosphorus halide compound, an inert water immiscible organic solvent and/or diluent is employed in an amount such that 5 to 50% strength solution of the neutral phosphorous acid aryl ester is formed and after the reaction, the organic phase is separated off and the phosphorous acid aryl ester formed is isolated by removing the solvent and/or diluent.

10 Claims, No Drawings

PROCESS FOR THE PREPARATION OF NEUTRAL PHOSPHOROUS ACID ARYL ESTERS

The present invention relates to a process for the preparation of neutral phosphorous acid aryl esters by reacting phosphorus trihalides, phosphorous acid monoester dihalides or phosphorous acid diester halides with hydroxyaryl compounds.

It is known that triphenyl phosphites may be prepared by reacting phosphorus trihalides with particular phenols in the presence of a catalyst and of an inert organic diluent, preferably at temperatures of about 150° to 200° C. (DE-AS (German Published Specification) No. 2,028,878).

It is also known that triaryl phosphites may be prepared from phenol and phosphorus trichloride by a process in which the three stages of the reaction are allowed to proceed separately in sections of the apparatus which are connected in series and differ from one another in that the pressures decrease and the temperatures increase (DE-AS (German Published Specification) No. 2,007,070).

The disadvantage of the reactions described above are the high temperatures at which the reactions are carried out (compare the examples of DE-AS (German Published Speicification) No. 2,028,878) and which are necessary, especially towards the end of the reaction, in order to remove, from the reaction mixture, the hydrogen chloride gas formed (compare the examples of DE-AS (German Published Specification) No. 2,007,070).

Moreover, very long reaction times are necessary in order to achieve high yields, whereupon the formation of by-products is promoted and the quality of the product (for example colour) is impaired. Purification operations which require technical effort, such as distillation in vacuo of the esters, which in some cases are high-boiling, or recrystallization of the esters in suitable solvents, are necessary in order to obtain pure products which, in particular, are free from catalysts.

The formation of hydrogen chloride gas is a particular disadvantage of the processes described above. Because of the corrosion thereby caused, the materials of the unit in which the esters are prepared must fulfil high requirements. In addition, special devices in which the hydrogen chloride gas formed are collected and absorbed, for example in water, must also be available.

A process has now become available for the preparation of a neutral phosphorous acid aryl ester of the general formula (I)

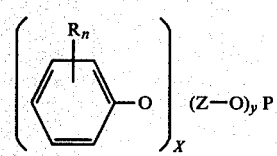

in which
each R independently represents hydrogen, halogen, a nitrile group, an alkyl, alkoxy or phenoxy radical or an optionally fused phenyl radical, or a fused aromatic ring system which is interrupted by hetero-atoms, n denotes an integer from 1 to 5, and the radicals R can be identical or different, X represents an integer from 1 to 3, Z represents an alkyl radical or a radical of the formula

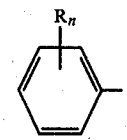

wherein
R and n have the above meaning, and
Y represents 1 if x represents 2, or 2 if x represents 1, or 0 if x represents 3, by contacting a phosphorus trihalide, phosphorous acid monoester dihalide or phosphorous acid diester halide of the formula (II), (III) or (IV)

| PHal$_3$ | ZOPHal$_2$ | (ZO)$_2$PHal |
|---|---|---|
| (II) | (III) | (IV) | in which
Z has the meaning already given in the case of formula (I) and
Hal represents fluorine, chlorine and/or bromine, with hydroxyaryl compounds of the general formula (V)

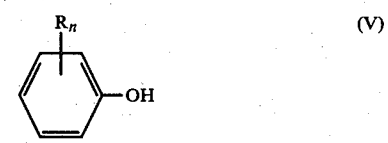

in which
R and n have the meanings already given in the case of formula (I),
which is characterized in that an excess (stoichiometric) of hydroxyaryl compound and an excess (stoichiometric) of aqueous alkali metal hydroxy solution or suspension and/or alkaline earth metal hydroxy solution or suspension is employed, relative to the phosphorus halide compound, an inert organic water immiscible solvent and/or diluent present in an amount such that 5 to 50% strength by weight solution of the neutral phosphorous acid aryl ester is formed, and, after the reaction, the organic phase is separated off and the phosphorous acid aryl ester formed is isolated by removing the solvent and/or diluent.

Examples of possible alkyl radicals are those with 1 to 20 carbon atoms, preferably with 1 to 4 carbon atoms. As examples there are mentioned: methyl, ethyl, n-propyl, iso-propyl, n-butyl, iso-butyl, tert.-butyl, n-pentyl, n-hexyl, n-octyl, n-decyl and n-dodecyl. Alkyl radicals with 3 to 4 carbon atoms, such as isopropyl, iso-butyl and tert.-butyl, are particularly preferred.

Examples of possible alkoxy radicals are those with 1 to 20 carbon atoms, preferably with 1 to 4 carbon atoms. As examples there are mentioned: methoxy, ethoxy, n-propoxy, iso-propoxy, n-butoxy, iso-butoxy, tert.-butoxy and hexyloxy.

Alkoxy radicals with 1 to 3 carbon atoms, such as methoxy, ethoxy and iso-propoxy, are particularly preferred.

Examples of possible phenoxy radicals are those with 6 to 12 carbon atoms, preferably the unsubstituted phenoxy radical.

Examples of possible optionally fused phenyl radicals are those with 6 to 12 carbon atoms, preferably with 6 carbon atoms, the unsubstituted phenyl radical being preferred.

Examples of possible fused ring systems interrupted by hetero-atoms, such as nitrogen, sulphur or oxygen, are those with 8 to 9 carbon atoms. As examples there are mentioned: 8-hydroxyquinoline, 7-hydroxythionaphthene and 7-hydroxybenzofurane.

Phosphorus trihalides of the formula (II) which can be employed in the process according to the invention are, for example, phosphorus trichloride or phosphorus tribromide. Phosphorus trichloride is preferably employed.

Examples of possible phosphorous acid monoester dihalides of the formula (III) and phosphorous acid diester halides of the formula (IV) are those such as can be obtained by reacting phosphorus trihalides with an excess of organic hydroxy compounds. As examples there are mentioned: phosphorous acid monoethyl ester dichloride, phosphorous acid mono-2-ethylhexyl ester dichloride and phosphorous acid diphenyl ester monochloride.

In the process according to the invention, reaction partners for the phosphorus compounds of the formulae (II) to (IV) are hydroxyaryl compounds of the general formula

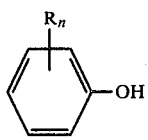

(V)

in which
R and n have the meaning given in the case of formula (I).

As hydroxyaryl compounds of the formula (V) there are mentioned, for example: phenol, o-, m- and p-cresol, o-, m- and p-isopropylphenol, o-, m- and p-sec.-butylphenol, o-, m- and p-tert.-butylphenyl, p-iso-octylphenyl, o-, m- and p-n-nonylphenol, 2-ethoxyphenol, 4-phenoxyphenol, 4-phenylphenol, o- and p-chlorophenol, o- and p-bromophenol, sym.-tribromophenol, α-naphthol and 8-hydroxyquinoline.

The hydroxyaryl compounds can be employed, in the process according to the invention, individually or in the form of any desired mixtures with one another.

An excess of hydroxyaryl compound, based on one equivalent of phosphorus halide compound, is usually employed in the process according to the invention. For example, 1.01 to 4 mols, preferably 1.02 to 1.5 mols, of hydroxyaryl compound can be employed per equivalent of phosphorus halide compound.

Solvents and/or diluents which are employed in the process according to the invention are organic compounds which are inert under the reaction conditions and which are not water-miscible. As examples there are mentioned: benzene, toluene, xylene and halogenated hydrocarbons with 1to 10 carbon atoms, preferably with 1 to 6 carbon atoms, such as chlorobenzene, methylene chloride and 1,2-dichloroethane. Toluene, chlorobenzene and/or methylene chloride are preferably employed in the process according to the invention.

In a particularly advantageous embodiment of the process according to the invention, the hydroxyaryl compounds which participate in the reaction or the esters formed in the reaction are used as the solvent. It is a prerequisite of this embodiment that the melting points or pour points of these compounds are below the reaction temperature.

The solvents and/or diluents are employed in amounts such that 5 to 50% strength by weight solutions, preferably 15 to 30% strength by weight solutions, of the neutral phosphorous acid aryl esters in the solvents and/or diluents employed are formed.

It is a particular characteristic of the process according to the invention that the reaction is carried out in the presence of an aqueous alkali metal hydroxide solution or suspension and/or an alkaline earth metal hydroxide solution or suspension.

Alkali metal hydroxides and/or alkaline earth metal hydroxides which can be employed are, for example, the hydroxides of sodium, potassium and/or calcium. Sodium hydroxide is preferably employed in the process according to the invention.

The alkali metal hydroxide and/or alkaline earth metal hydroxide is employed in excess, relative to the phosphorus halide compound. For example at least 1.01 mols and say 1.01 mols to 2 mols, preferably 1.01 to 1.25 mols, of alkali metal hydroxide and/or alkaline earth metal hydroxide can be employed per equivalent of phosphorus halide compound.

The contents of pure alkali metal hydroxide and/or alkaline earth metal hydroxide in the aqueous alkali metal hydroxide solutions or suspensions and/or alkaline earth metal hydroxide solutions or suspensions can vary greatly. Concentrations in the range from 1 to 60% by weight are preferably chosen.

Since the process according to the invention is carried out in the presence of excess alkali metal hydroxide and/or alkaline earth metal hydroxide, the pH value of the reaction mixture is in the basic range. The pH value depends on the acidity of the hydroxyaryl compound used and of the particular excess of alkali metal hydroxide and/or alkaline earth metal hydroxide.

The use of high concentrations of alkali metal hydroxide and/or alkaline earth metal hydroxide in the aqueous solution or suspension represents a particular embodiment of the process according to the invention. In this case, the alkali metal halide and/or alkaline earth metal halide formed during the reaction separates out in the form of a solid when the saturation limit is reached, and can be separated off, when the reaction has ended, by known processes, for example by filtration or centrifugation, for example using a rotary filter, trailing blade centrifuges or similar equipment.

An increase in the amounts of aqueous reaction phase by adding saturated alkali metal halide solutions and/or alkaline earth metal halide solutions, preferably the aqueous reaction phase which is obtained after separating off the alkali metal halide and/or alkaline earth metal halide which has precipitated and the organic phase, can have a favourable effect on the reaction.

Pollution of the effluents by alkali metal halide and/or alkaline earth metal halide is considerably reduced by these process variants.

It has been found that, as a rule, the reaction proceeds with an adequate yield and at a sufficient rate without catalysts. However, the rate of reaction, in particular, can be increased by catalysts. Examples of possible catalysts which can increase, in particular, the rate of reaction are tertiary amines and quaternary ammonium, phosphonium and sulphonium compounds, such as triethylamine, n-tributylamine or tetramethylammonium hydroxide. The catalyst concentration can be varied within wide limits; 0.001 to 0.1 mol of catalyst can preferably be used per mol of hydroxyaryl compound employed.

The reaction temperatures of the process according to the invention can vary within wide limits. The process according to the invention can be carried out particularly advantageously at temperatures of 5° to 95° C., preferably at 10° to 50° C. The reaction times are usually about 5 to 90 minutes, depending on the reaction procedure and the temperature at which the reaction is carried out, and they can be shortened by using catalysts.

The process according to the invention can be carried out, for example, by a procedure in which the hydroxyaryl compound is mixed with the alkali metal hydroxide solution or suspension and/or alkaline earth metal hydroxide solution or suspension, if appropriate with the addition of water or with the addition of a saturated alkali metal halide solution or suspension and/or alkaline earth metal halide solution or suspension, in a stirred kettle which can be cooled, and the mixture is combined, whilst stirring vigorously, with the phosphorus trihalide, phosphorous acid monoester dihalide or phosphorous acid diester halide, which is dissolved in the organic inert solvent, at a rate such that the reaction temperature can be controlled by cooling.

When the reaction has ended, the reaction mixture can be worked up in a known manner. The emulsion present after the reaction can be freed, if necessary, from precipitated alkali metal halides and/or alkaline earth metal halides by filtration and can then be separated. The organic phase can then be washed, for example in mixer/separator apparatuses or separators, with acid and then with water until free from electrolyte. The inert organic solvent can, for example, be removed by distillation.

The residue which remains can be subjected to further purification, for example by distillation or crystallisation.

Separate purification of the resulting phosphorous acid aryl esters can, however, be omitted if pure starting compounds are used and the reaction is carried out under an inert gas atmosphere, such as nitrogen. It is then sufficient to evaporate off the organic solvent, the pure, light-coloured phosphorous acid aryl esters being obtained as residues.

The process according to the invention can be carried out continuously or discontinuously.

Neutral phosphorous acid aryl esters can be prepared in good yields and high purities by the process according to the invention.

The reaction temperatures of the process according to the invention can be kept low and the reaction times can be kept short, which makes the process particularly economic.

Moreover, no hydrogen chloride gas is liberated in the process according to the invention. Special devices in which the hydrogen chloride gas must be collected and absorbed are thereby dispensed with. In addition, it is not absolutely necessary for the materials of the unit in which the phosphorous acid aryl esters are prepared according to the invention to be particularly corrosion-resistant. This factor also contributes to the profitability of the process according to the invention.

Furthermore, it is exceptionally surprising that neutral phosphorous acid aryl esters are formed in good yields in the reaction, according to the invention, of phosphorus trihalides, phosphorous acid monoester dihalides or phosphorous acid diester halides with hydroxyaryl compounds even though an excess of aqueous alkali metal hydroxy solution or suspension and/or alkaline earth metal hydroxy solution or suspension is employed.

In fact, it was to be expected that the phosphorous acid aryl esters formed would be hydrolyzed immediately in the presence of alkalis to give the phosphorous acid diester or monoester, such as is described in Houben-Weyl, Methoden der organischen Chemie (Methods of Organic Chemistry), Volume VII/2, pages 7, 30, 31 and 79 (1964).

The neutral phosphorous acid aryl esters prepared according to the invention can be used, above all, as stabilizers for polymers in order to protect these against degradation, heat, light or the effects of oxygen or oxygen-containing compounds (Kirk-Othmer Encyclopaedia of Chemical Technology, 2nd edition, Volume 17, page 519).

The following examples are intended to illustrate the process according to the invention without, however, restricting it to these examples.

EXAMPLE 1

169.4 g of phenol, 150 ml of toluene, 120 g of water and 155.6 g of 45% strength sodium hydroxide solution (1.75 mols) are initially introduced into a threenecked flask with a stirrer, dropping funnel and thermometer. A solution of 68.7 g of phosphorus trichloride and 100 ml of toluene is added dropwise in the course of 15 minutes, whilst stirring vigorously. The temperature is kept between 25° and 30° C. by cooling. The mixture is subsequently stirred at 30° C. for 30 minutes. The phases are separated. The organic layer is extracted by washing 3 times with water. The toluene is distilled off and the residue is fractionated under a high vacuum. 132 g of triphenyl phosphite are obtained. The yield is 86% of theory; the purity is >99%.

EXAMPLES 2 TO 4

These examples were carried out as described in Example 1. The most important parameters and the results are summarised in the following table.

| Example | Mols of hydroxyaryl compound per mol of PCl$_3$ | | Mols of NaOH per mol of PCl$_3$ | % of ester in toluene solution | Yield % of theory |
| --- | --- | --- | --- | --- | --- |
| 2 | 3.6 mols | 2,4-di-tert.-butylphenol | 3.5 mols | 40.5 | 85 |
| 3 | 3.6 mols | 2,4,6-tri-isopropyl-phenol | 3.5 mols | 39 | 77 |
| 4 | 2.4 mols | phenol* | 2.33 mols* | 37 | 86 |

*in each case per mol of phosphorous acid mono-2-ethyl-hexyl ester dichloride
The purities of the products are >99%.

What is claimed is:
1. In a process for the preparation of a neutral phosphorous acid aryl ester of the general formula

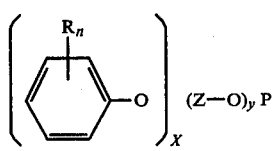 (I)

in which
each R independently represents hydrogen, halogen, a nitrile group, an alkyl, alkoxy or phenoxy radical or an optionally fused phenyl radical, or a fused aromatic ring system which is interrupted by hetero-atoms, n denotes an integer from 1 to 5, and the radicals R can be identical or different, X represents an integer from 1 to 3, Z represents an alkyl radical or a radical of the formula

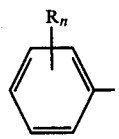

wherein
R and n have the above meaning, and
y represents 1 if x represents 2, or 2 if x represents 1, or 0 if x represents 3, by contacting a phosphorus trihalide, phosphorous acid monoester dihalide or phosphorous acid diester halide of the formula (II), (III), or (IV)

| $PHal_3$ | $ZOPHal_2$ | $(ZO)_2PHal$ |
|---|---|---|
| (II) | (III) | (IV) | in which
Z has the meaning already given in the case of formula (I) and

Hal represents fluorine, chlorine and/or bromine, with a hydroxyaryl compound of the general formula

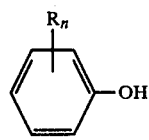 (V)

in which
R and n have the meanings already given in the case of formula (I), the improvement wherein an excess of (stoichiometric) of hydroxyaryl compound and an excess (stoichiometric) of aqueous alkali metal hydroxide solution or suspension and/or alkaline earth metal hydroxide solution or suspension are employed, relative to the phosphorus halide compound, an inert organic water-immiscible solvent and/or diluent being present in an amount such that 5 to 50% strength by weight solution of the neutral phosphorous acid aryl ester is formed, and, after the reaction, the organic phase is separated off and the phosphorous acid aryl ester formed is isolated by removing the solvent and/or diluent.

2. Process according to claim 1, wherein the reaction is carried out at temperatures of 5° to 95° C.

3. Process according to claim 1, wherein the reaction is carried out at temperatures of 10° to 50° C.

4. Process according to claim 1, wherein the reaction is carried out with an excess of hydroxyaryl compounds of 1.01 to 4 mols per equivalent of phosphorus halide compound.

5. Process according to claim 1, wherein the reaction is carried out with an excess of aqueous alkali metal hydroxide solution or suspension and/or alkaline earth metal hydroxide solution or suspension of 1.01 to 2 mols per equivalent of phosphorus halide compound.

6. Process according to claim 1, wherein phosphorus trichloride is employed as the phosphorus halide compound.

7. Process according to claim 1, wherein an alkali metal hydroxide solution or suspension is employed and sodium hydroxide is the alkali metal hydroxide.

8. Process according to claim 1, wherein toluene, chlorobenzene and/or methylene chloride is employed as inert organic water-immiscible solvents and/or diluents.

9. A process according to claim 1, wherein a phosphorous acid monoester dihalide is reacted with said hydroxyaryl compound.

10. A process according to claim 1, wherein a phosphorous acid diester halide is reacted with said hydroxy aryl compound.

* * * * *